United States Patent [19]

Steckhan et al.

[11] Patent Number: 4,526,661
[45] Date of Patent: Jul. 2, 1985

[54] ELECTROCHEMICAL HYDROGENATION OF NICOTINAMIDE ADENINE DINUCLEOTIDE

[75] Inventors: Eberhard Steckhan, Meckenheim; Rainer Wienkamp, Muenster, both of Fed. Rep. of Germany

[73] Assignee: BASF Aktiengesellschaft, Del.X

[21] Appl. No.: 499,261

[22] Filed: May 31, 1983

[30] Foreign Application Priority Data

Jun. 5, 1982 [DE] Fed. Rep. of Germany ....... 3221339

[51] Int. Cl.$^3$ ............................................. C25B 3/04
[52] U.S. Cl. ..................................... 204/73 R; 204/74
[58] Field of Search ......................... 204/72, 73 R, 74

[56] References Cited

U.S. PATENT DOCUMENTS 4,318,784  5/1982  Higgins et al. .................. 204/73 R
4,326,932  4/1982  Fröling ............................ 204/73 R
4,381,978  5/1983  Gratzel et al. ...................... 204/72

OTHER PUBLICATIONS

Angew Chem., 93, (1981), No. 10, pp. 897–898.
J. Org. Chem., 1981, 46, 4100–4101; 4622–4623.

Primary Examiner—Howard S. Williams
Assistant Examiner—Terryence Chapman
Attorney, Agent, or Firm—Keil & Weinkauf

[57]   ABSTRACT

Nicotinamide adenine dinucleotide (NAD$^\oplus$) is electrochemically hydrogenated to NADH in aqueous solution and in the presence of a metal complex as an electron carrier.

3 Claims, No Drawings

ELECTROCHEMICAL HYDROGENATION OF NICOTINAMIDE ADENINE DINUCLEOTIDE

The present invention relates to a process for the electrochemical hydrogenation of nicotinamide adenine dinucleotide (NAD⊕).

It is known that, in the body, NAD⊕ acts as a hydrogen carrier in many enzymatic processes involving dehydrogenation and hydrogenation. In the case of redox reactions, the coenzyme NAD⊕/NADH reacts in the following manner:

$$NAD^\oplus + 2H = \rightarrow NADH + H^\oplus$$

A very large number of enzymes and micro-organisms are capable of reducing unsaturated compounds in the presence of NADH. These reductions, in which NADH acts, as described, as a coenzyme, take place in a wide range of substrates and have the advantage of high stereospecificity. It is therefore desirable to employ this advantageous mode of action for a commercially usable reduction of unsaturated compounds, in particular for the preparation of chiral molecules. However, such a possibility can be realised economically only when NADH can be regenerated in a simple manner from the NAD⊕ formed in the reduction.

Electrochemical reduction of NAD⊕ to NADH at −1.1 volt, based on the calomel electrode, essentially gives dimers which have no enzymatic action. Since even at a very negative potential of −1.8 volt, based on the calomel electrode, NADH is formed in a yield of only 50%, together with inactive dimers and isomers, direct electrochemical reduction is virtually useless as a method of regenerating NAD⊕.

It has therefore been proposed that NAD⊕ be regenerated by an indirect electrochemical reduction in which the electrolysis is carried out in the presence of an electron carrier and of an additional enzyme which catalyzes electron transfer to the coenzyme NAD⊕.

Thus, processes in which methyl viologen or trans-4,5-dihydroxy-1,2-dithiane is used as an electron carrier have been described in Angew. Chem. 98 (1981), 897, in J. Org. Chem. 46 (1981), 4,622 and in J. Org. Chem. 46 (1981), 4,100. However, these methods have the disadvantage that the enzymes required for catalysis of the electron transfer are sensitive, difficult to purify and expensive to isolate.

We have found that the electrochemical hydrogenation of nicotinamide adenine dinucleotide (NAD⊕) to NADH in aqueous solution and in the presence of an electron carrier can be carried out substantially more advantageously if a metal complex is used as the electron carrier.

Particularly suitable metal complexes are those having a reduction potential which is not more negative than −1.3 volt, preferably not more negative than −0.9 volt, based on the Ag/AgCl electrode. Metal complexes of the stated types contain, as the central atom, for example $Rh^I$, $Rh^{III}$, $Ru^I$, $Ru^{III}$, $Ir^I$, $Ir^{III}$, $Fe^{II}$, $Fe^O$, $Ni^{II}$, $Ni^O$, $Co^{III}$ or $Co^I$ and, as ligands, for example 2,2'-bipyridine, 4,4'-dimethyl-2,2'-bipyridine, 1,10-phenanthroline, 2,2',6',2''-terpyridine, a tetraazamacrocyclic structure, a porphyrin, a phthalocyanine or NO.

Specific examples of such metal complexes, of which those having organic ligands are preferred, are aquocobalamine, $[Rh(bipy)_3]^{3\oplus}X_3^\ominus$, $[Rh(bipy)_2]^{3\oplus}X_3^\ominus$, $[Rh(bipy)_2(H_2O)_2]^{3\oplus}X_3^\ominus$, $[Ni(PPh_3)_2]^{2\oplus}X_2^\ominus$, $[Rh(bipy)_2(H_2O)]^\oplus X^\ominus$, $[Ru(bipy)_3]^{3\oplus}X_3^\ominus$, $[Rh(bipy)_2(OH)_2]^\oplus X^\ominus$, $[Fe(NO)_2Cl]_2$, $[Rh(bipy)(H_2O)]^\oplus X^\ominus$, $[Co(NO)_2Br]_2$, in which X is an anion, eg. Cl.

The novel electrochemical process is preferably carried out in a compartmented cell at not more than 70° C., advantageously at from 10° to 50° C., and at a pH of from 5 to 10. The electrodes used are composed of materials which are conventionally employed for electrosyntheses. Thus, for example, a suitable cathode is one comprising a metal, such as lead, copper, iron or nickel, or graphite, and a suitable anode is one made of platinum or graphite. The current density is, for example, from 1 to 100 mA/cm², and the cathode potential is, for example, not more than −1.3 volt, preferably from −0.5 to −0.9 volt, based on the Ag/AgCl electrode.

The electrolysis is carried out in an aqueous solution, which may also contain, for example, a solubilizer, ie. a water-miscible organic solvent, eg. an alcohol, such as methanol or ethanol, or an ether, such as dioxane or dimethoxyethane.

For example, the reaction may be carried out in an aqueous solution of a tris-HCl buffer, ie. a solution of tris-(hydroxymethyl)-aminomethane which has been brought to the desired pH by the addition of hydrochloric acid.

The electrochemical hydrogenation of NAD⊕ with the aid of the stated electron carriers is advantageously carried out in the presence of the unsaturated compound which it is intended to reduce by means of the regenerated NADH, as well as in the presence of an enzyme which catalyzes the reduction of the unsaturated compound by NADH.

Examples of suitable unsaturated compounds are ketones, eg. cyclohexanone, methylcyclohexanone, ethylcyclohexanone, 2-norbornanone, bicyclo[3.2.1]octan-2-one or acetophenone, and aldehydes, ketocarboxylic acids or compounds possessing C=C double bonds.

Examples of suitable enzymes are all known NADH- and NADPH (nicotinamide adenine dinucleotide phosphate)dependent oxido-reductases, ie. alcohol dehydrogenases, such as HLADH (horse liver alcohol dehydrogenase) or amino acid dehydrogenases.

The electrochemical hydrogenation of NAD⊕ to NADH can be carried out particularly advantageously by the process according to the invention. Thus, for example, the formation of dimers of NAD⊕ is substantially prevented, and, furthermore, the process can also be carried out in the absence of enzymes which were added in conventional methods in order to catalyze electron transfer to NAD⊕.

The Examples which follow illustrate the novel process for the indirect electrochemical reduction of NAD⊕ to NADH with the aid of Rh(bipy)$_2$⊕ as an electron carrier; the compound reduced is cyclohexanone which, in the presence of the enzyme HLADH (horse liver alcohol dehydrogenase), is converted to cyclohexanol. The reactions which take place in the cathode space during this process may be represented by the following diagram:

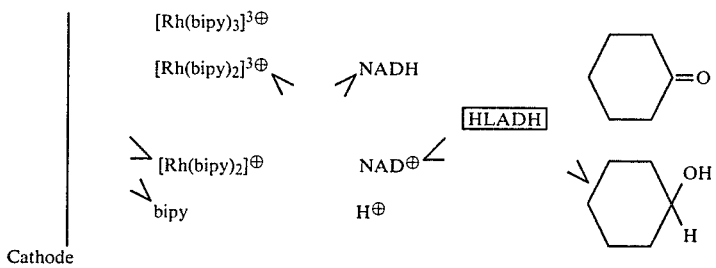

During this process, the electron carrier tris-[2,2'-bipyridyl]-rhodium trichloride accepts electrons at the cathode and is hence converted to bis-[2,2'-bipyridyl]-rhodium chloride, in accordance with the following equation:

under an argon atmosphere during electrolysis. The initial current was from 10 to 20 mA.

Examples 1 and 2 in the following table were carried out by a batchwise procedure, ie. the enzyme HLADH and cyclohexanone were added to the catholyte only after the indirect electrochemical hydrogenation of NAD⊕ to NADH, and the cyclohexanol was then determined. In the continuous procedure according to Examples 3, 4 and 5 in the table, electrolysis was carried out in the presence of HLADH and cyclohexanone, and the cyclohexanol was determined by gas chromatography.

The amounts of starting materials and the results are shown in the table below.

TABLE

| Example | Rh(bipy)$_3$Cl$_3$ mg (mmole) | NAD⁺ mg (mmole) | Cyclohexanone mg (mmole) | HLADH mg (mmole) | Cyclohexanol mg (mmole) | Number of cycles NAD⁺/NADH | Rh$^{3+}$/Rh⁺ |
|---|---|---|---|---|---|---|---|
| 1 | 384 (0.5) | 332 (0.5) | 59 (0.6) | 2.0 (2.4 × 10⁻⁵) | 25 (0.25) | 0.5 | 0.5 |
| 2 | 230 (0.3) | 398 (0.6) | 73.5 (0.75) | 2.0 (2.4 × 10⁻⁵) | 29 (0.29) | 0.5 | 0.5 |
| 3 | 115 (0.15) | 100 (0.15) | 96 (0.98) | 1.1 (1.3 × 10⁻⁵) | 33 (0.33) | 2.2 | 2.2 |
| 4 | 307 (0.4) | 133 (0.2) | 171 (1.74) | 3.9 (4.6 × 10⁻⁵) | 42 (0.42) | 2.1 | 1.0 |
| 5 | 192 (0.25) | 66.5 (0.1) | 110 (1.12) | 2.0 (2.4 × 10⁻⁵) | 29 (0.29) | 2.9 | 1.1 |

(Each cycle comprises a single regeneration of NADH from the NAD⊕ employed)

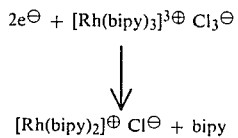

EXAMPLES

Electrolysis was carried out at room temperature, pH 9 and a potential of −950 mv, based on an Ag/AgCl electrode, in a compartmented electrolysis cell possessing a graphite cathode with a surface area of 6 cm², a platinum anode and a glass frit as the diaphragm. The reference electrode used comprised an Ag/AgCl electrode in saturated aqueous potassium chloride.

The anolyte used was a 0.1 molar aqueous solution of tris-HCl buffer, which was brought to pH 9 with concentrated hydrochloric acid. The catholyte comprised a stock solution which was the same as the solution used for the anolyte, together with Rh(bipy)$_3$Cl$_3$, NAD⊕, cyclohexanone and HLADH in the amounts stated in the table below.

The electrolysis apparatus was flushed with argon before the cyclohexanone was added, and was kept

We claim:

1. In an electroylsis process wherein nicotinamide adenine dinucleotide (NAD⁺) is hydrogenated to (NADH) by an indirect electrochemical reduction in which the electrolysis is carried out in the presence of an electron carrier, the improvement which comprises: employing as the electron carrier a metal complex having a reduction potential which is not more negative than −1.3 volt, based on a reference electrode consisting of an Ag/AgCl electrode in saturated aqueous potassium chloride, and wherein the electrolysis is carried out in a cell at a temperature of from about 10° to 70° C., a pH of from about 5 to 10 and a current density of from 1 to 100 mA/cm².

2. A process as claimed in claim 1, wherein the metal complex used possesses organic ligands.

3. A process as claimed in claim 1, wherein the metal complex used contains, as the central atom, Rh$^I$, Rh$^{III}$, Ru$^I$, Ru$^{III}$, Ir$^I$, Ir$^{III}$, Fe$^{II}$, Fe$^O$, Ni$^{II}$, Ni$^O$, Co$^{III}$ or Co$^I$ and, as ligands, 2,2'-bipyridine, 4,4'-dimethyl-2,2'-bipyridine, 1,10-phenanthroline, 2,2',6',2''-terpyridine, a tetraazamacrocyclic structure, a porphyrin, a phthalocyanine or NO.

* * * * *